United States Patent [19]

Evans

[11] 4,404,140

[45] Sep. 13, 1983

[54] MANUFACTURE OF ALKYLANTHRAQUINONES

[75] Inventor: William L. Evans, Turnersville, N.J.

[73] Assignee: E. I. Du Pont de Nemours and Company, Wilmington, Del.

[21] Appl. No.: 314,869

[22] Filed: Oct. 26, 1981

[51] Int. Cl.$^3$ ............................................. C07C 49/68
[52] U.S. Cl. ................................................... 260/369
[58] Field of Search ........................................ 260/369

[56] References Cited

U.S. PATENT DOCUMENTS 3,032,560  5/1962  Dawsey ............................... 260/369
4,035,396  7/1977  Milano ................................ 260/369
4,045,456  8/1977  Merger et al. ...................... 260/369

*Primary Examiner*—Delbert E. Gantz
*Assistant Examiner*—Raymond Covington

[57] ABSTRACT

A process for preparing alkylanthrquinones wherein the alkyl group contains from 2 to 5 carbon atoms such as 2-ethylanthraquinone, 2-t-amylanthraquinone or 2-t-butylanthraquinone by ring closure from the corresponding alkylbenzoylvenzoic acid is disclosed. The process involves adding a solution of the alkylbenzoylbenzoic acid to 100% concentrated sulfuric acid or up to 12% oleum, distilling off the solvent at from 20° to 60° C., heating the remaining solution to from 80° to 95° C. and preferably from 83° to 87° C. for 3 to 5 hours, diluting the remaining reaction mixture with water and separating the alkylanthraquinone product.

10 Claims, No Drawings

MANUFACTURE OF ALKYLANTHRAQUINONES

BACKGROUND OF THE INVENTION

FIELD OF THE INVENTION

The present invention relates to a process of condensing phthalic anhydride with an alkylbenzene to form an alkylbenzoylbenzoic acid, followed by ring closure to form an alkylanthraquinone.

Alkylanthraquinones find utility in the well-known working solution process for preparing hydrogen peroxide in which a supported metal, such as palladium, catalyst is used to reduce the alkylanthraquinone to the corresponding alkylanthrahydroquinone. These supported metal catalysts are readily poisoned by impurities including those often associated with the production of alkylanthraquinones. Normally these impurities are removed during the manufacture of alkylanthraquinones by the time consuming and costly procedures of vacuum distillation or crystallization.

Alkylbenzoylbenzoic acids, which are the starting material for the process of the present invention, are customarily prepared by a Friedel-Crafts reaction from phthalic anhydride and an alkylbenzene. The reaction is usually performed in an inert solvent of the type commonly referred to as Friedel-Crafts solvents such as chlorobenzene, dichlorobenzene, trichlorobenzene, tetrachloroethane, chloroform, carbon tetrachloride, carbon disulfide, etc.

Generally the alkylbenzoylbenzoic acid is converted to the corresponding alkylanthraquinone by heating it in sulfuric acid or oleum for from three to five hours. Stoichiometry is critical as many side reactions are possible. Furthermore, both the starting material and product can be sulfonated. The intermediate carbonium ion which is formed can ring close to the desired product or alkylate neutral species leading to high boiling tarry substances. Conditions must be balanced to optimize yield and minimize side reactions.

U.S. Pat. No. 3,032,560 discloses the preparation of amylanthraquinone by heating one part of 2(4'-amylbenzoyl)benzoic acid at from 65° to 95° C. in the presence of at least 5 parts of oleum containing from 5 to 10% sulfur trioxide.

This type of process is characterized by low yields, 71%, probably because of poor dispersion of the solid in the oleum producing zones of unfavorable stoichiometry which leads to tarry by-product formation. Purification of the alkylanthraquinone crude by distillation or crystallization is necessary to remove these tarry by-products.

U.S. Pat. No. 4,035,396 discloses preparing alkylanthraquinones by heating at 85° to 95° C. one part of an alkylbenzoybenzoic acid dissolved in at least five parts of trichlorobenzene in the presence of oleum. This process is an improvement over the above process since the solvent provides a more uniform dispersion of the alkylbenzoylbenzoic in the sulfuric acid or oleum and a more uniform stoichiometry is achieved. This process usually requires a high boiling solvent which exerts a high solvating action on the alkylbenzoylbenzoic acid. A chlorinated aromatic such as trichlorobenzene is commonly used as the solvent. However, this and similar solvents can be sulfonated and react in other ways with the oleum and reactants to produce tars. Purification by distillation or crystallization is necessary to remove these tars.

SUMMARY OF THE INVENTION

The present invention involves adding a solution of an alkylbenzoylbenzoic acid, wherein the alkyl group contains from 2 to 5 carbon atoms, in a low boiling solvent such as methylene chloride, to concentrated sulfuric acid or oleum removing the solvent by distillation and heating to effect ring closure and form the corresponding alkylanthraquinone. After dilution with water, the alkylanthraquinone in the reaction mass is extracted with an organic solvent.

DETAILED DESCRIPTION

The present invention relates to a process for the manufacture of alkylanthraquinones, preferably 2-alkylanthraquinones. The most preferred 2-alkylanthraquinones are 2-t-amylanthraquinone, 2-t-butylanthraquinone and 2-ethylanthraquinone.

A solution of an alkylbenzoylbenzoic acid in methylene chloride or other suitable solvent is added to 100% sulfuric acid or up to 12% oleum to effect ring closure to the corresponding alkylanthraquinone. Generally the solution will contain from 10 to 40% by weight alkylbenzoylbenzoic acid, with from 15 to 30% by weight being the preferred range. Generally from 7 to 15 parts by weight of sulfuric acid or oleum should be used per part by weight of alkylbenzoylbenzoic acid being reacted with from 9 to 12 parts by weight being the preferred range. The temperature of the solution is not critical and will be from 10° to 60° C. The sulfuric acid or oleum may be at any convenient temperature such as 10° to 60° C. when the solution of alkylbenzoylbenzoic acid is added thereto. The solvent is distilled off rapidly prior to any appreciable amount of the ring closure reaction taking place. For practical considerations the solvent should dissolve at least 10% by weight of the alkylbenzoylbenzoic acid in solvent at 20° C. and be removable by distillation at from 20° to 60° C. Suitable solvents include but are not limited to methylene chloride, carbon tetrachloride, chloroform, perchloroethylene, and carbon disulfide. The solvent serves to uniformly distribute the alkylbenzoylbenzoic acid in the sulfuric acid or oleum, but does not interfere with the ring closure reaction, as is the case with the chlorinated aromatic solvents, because it is removed prior to the main ring closure reaction. After the solvent is removed the remaining mixture is heated to from 80° to 95° C. and preferably from 83° to 87° C. for from 3 to 5 hours and then drowned into water to dilute the sulfuric acid to from 10 to 40% by weight and preferably from 20 to 30% by weight. The alkylanthraquinone is extracted from the aqueous phase with a solvent such as an aromatic hydrocarbon solvent or a halogenated organic solvent. Generally the solvent will boil at from 40° to 250° C.

Because of the uniform dispersion of the alkylbenzoylbenzoic acid in the sulfuric acid or oleum by the process of the present invention, the yield is maximized and by-products minimized. Tar formation is so minimal that following drowning of the reaction mass in water the resulting slurry can be filtered in the case of 2-ethylanthraquinone or 2-t-butylanthraquinone and the crude washed free of impurities to give a dry product which is 99% pure and does not require distillation or crystallization. In the case of 2-t-amylanthraquinone the slurry can be extracted with any of a number of organic solvents such as methylene chloride, carbon tetrachloride, chloroform, alkylated aromatics, chlorinated aromatics such as chlorinated benzene. Following water and caustic washes the product can be recovered by steam distillation or evaporation to yield a high purity material (95+%). Generally no further purification is necessary.

EXAMPLE I

Ring closure of 2(4'-t-amylbenzoyl)benzoic acid to form 2-t-amylanthraquinone.

Three hundred and twenty-five parts of 1.0% oleum were added to a 500 ml 4-necked round bottom flask equipped with a stirrer, thermometer, dropping funnel, distillation head, ice water cooled condenser and heating mantle. The contents of the flask were stirred and maintained at 25±5° C. while 31.5 parts of 2-(4'-t-amylbenzoyl)benzoic acid as a 20–25% solution in methylene chloride was added to the flask over a 30 minute period. The contents of the flask were heated to 43°–45° C. and the methylene chloride distilled off and collected in a receiver over a one hour period. Then the contents of the flask were heated to 80°–85° C. and held for 4 hours. After the 4 hours the reaction mass was drowned into 1,000 parts of water with stirring while allowing the temperature to rise to 65° C. While at 65° C. the aqueous mixture is extracted with 180 parts of a mixture of aromatic hydrocarbons boiling at from 181°–210° C. and having a specific gravity at 15.56° C. of 0.887. The aqueous phase was separated and the hydrocarbon solution washed with 1,000 parts of water treated with sufficient 30% aqueous sodium hydroxide to give the aqueous phase, after washing, a positive test on Brilliant Yellow test paper. The hydrocarbon solution which contained 2-t-amylanthraquinone was separated and dried over anhydrous calcium chloride. The yield was 24.1 parts of 2-t-amylanthraquinone or about 82% of the theoretical yield.

EXAMPLE II

Ring closure of 2(4'-t-amylbenzoyl)benzoic acid to form 2-t-amylanthraquinone.

Three hundred and thirty parts of 2.0% oleum were added to a 500 ml 4-necked round bottom flask equipped with a stirrer, thermometer, dropping funnel, distillation head, ice water cooled condenser and heating mantle. The contents of the flask were stirred and maintained at 50°–60° C. while 31.45 parts of 2-(4'-t-amylbenzoyl)benzoic acid as a 20.75% solution in methylene chloride were added to the flask over a 30 minute period. Methylene chloride distilled off as the 2-(4-t-amylbenzoyl)benzoic acid solution was added and was collected in a receiver over a one hour period. Then the contents of the flask were heated to 85° C. and held for 5 hours. After the 5 hours the reaction mass was drowned into 1,000 parts of water with stirring while allowing the temperature to rise to 65° –70° C. While at 65°–70° C. the aqueous mixture is extracted with 100 parts of a mixture of aromatic hydrocarbons boiling at from 181°–210° C. and having a specific gravity at 15.56° C. of 0.887. The aqueous phase was separated and the hydrocarbon solution washed with 500 parts of water treated with sufficient 30% aqueous sodium hydroxide to give the aqueous phase after washing a positive test on Brilliant Yellow test paper. The hydrocarbon solution which contained 2-t-amylanthraquinone was separated and dried over anhydrous calcium chloride. The yield was 26 parts of 2-t-amylanthraquinone or about 88% of the theoretical yield.

EXAMPLE III

Ring closure of 2(4'-t-amylbenzoyl)benzoic acid to form 2-t-amylanthraquinone.

Three hundred and twenty-five parts of 5.4% oleum were added to a 500 ml 4-necked round bottom flask equipped with a stirrer, thermometer, dropping funnel, distillation head, ice water cooled condenser and heating mantle. The contents of the flask were stirred and maintained at 25±5° C. while 40.5 parts of 2-(4-t-amylbenzoyl)benzoic acid as a 20.75% solution in methylene chloride were added to the flask over a 30 minute period. Methylene chloride distilled off as the 2-(4'-t-amylbenzoyl)benzoic acid solution was added and was collected in a receiver over a one hour period. Then the contents of the flask were heated to 85° C. and held for 5 hours. After the 5 hours the reaction mass was drowned into 1,000 parts of water with stirring while allowing the temperature to rise to 65°–70° C. While at 65°–70° C. the aqueous mixture is extracted with 100 parts of a mixture of aromatic hydrocarbons boiling at from 181°–210° C. and having a specific gravity at 15.56° C. of 0.887. The aqueous phase was separated and the hydrocarbon solution washed with 500 parts of water treated with sufficient 30% aqueous sodium hydroxide to give the aqueous phase after washing a positive test on Brilliant Yellow test paper. The hydrocarbon solution which contained 2-t-amylanthraquinone was separated and dried over anhydrous calcium chloride. The yield was 28.7 parts of 2-t-amylanthraquinone or about 75% of the theoretical yield.

EXAMPLE IV

Ring closure of 2-(4-t-amylbenzoyl)benzoic acid to form 2-t-amylanthraquinone.

Three hundred and twenty-five parts of 100% sulfuric acid were added to a 500 ml 4-necked round bottom flask equipped with a stirrer, thermometer, dropping funnel, distillation head, ice water cooled condenser and heating mantle. The contents of the flask were stirred and maintained at 50°–60° C. while 28.4 parts of 2-(4'-t-amylbenzoyl)benzoic acid as a 20.75% solution in methylene chloride were added to the flask over a 30 minute period. Methylene chloride distilled off as the 2-(4'-t-amylbenzoyl)benzoic acid solution was added and was collected in a receiver over a one hour period. Then the contents of the flask were heated to 85° C. and held for 5 hours. After the 5 hours the reaction mass was drowned into 1,000 parts of water with stirring while allowing the temperature to rise to 65°–70° C. While at 65°–70° C. the aqueous mixture is extracted with 100 parts of a mixture of aromatic hydrocarbons boiling at from 181°–210° C. and having a specific gravity at 15.56° C. of 0.887. The aqueous phase was separated and the hydrocarbon solution washed with 500 parts of water treated with sufficient 30% aqueous sodium hydroxide to give the aqueous phase after washing a positive test on Brilliant Yellow test paper. The hydrocarbon solution which contained 2-t-amylanthraquinone was separated and dried over anhydrous calcium chloride. The yield was 22.8 parts of 2-t-amylanthraquinone or about 85% of the theoretical yield.

EXAMPLE V

Ring closure of 2-(4'-t-butylbenzoyl)benzoic acid to form 2-t-butylanthraquinone.

Thirteen hundred parts of 1.0% oleum were added to a 2000 ml 4-necked round bottom flask equipped with a stirrer, thermometer, dropping funnel, distillation head, ice water cooled condenser, and heating mantle. The contents of the flask were stirred and maintained at 45°–50° C. while 116 parts of 2-(4'-t-butylbenzoy)benzoic acid as a 20.25% solution in methylene chloride were added to the flask over a 60 minute period. Methylene chloride was distilled off as the 2-(4'-t-butylbenzoyl)benzoic acid solution was added and was collected in a receiver. Then the contents of the flask were heated to 85° C. and held 4 hours. After the 4 hours the reaction mass was drowned into 3000 parts of water with stirring while allowing the temperature to rise to 85° C. The resultant slurry was allowed to cool to room temperature overnight. The solid which separated was filtered and washed with 8000 parts water until the washings were negative to Congo Red Test paper. The solid was washed with 2000 parts of 3% NaOH solution followed by 8000 parts water. The yield was 95 parts of 2-t-butylanthraquinone or about 88% of the theoretical yield.

EXAMPLE VI

Ring closure of 2-(4'-t-amylbenozoyl)benzoic acid to form 2-t-amylanthraquinone.

Three hundred and thirty parts of 2.0% oleum were added to a 500 ml 4-necked round bottom flask equipped with a stirrer, thermometer, dropping funnel, distillation head, ice water cooled condenser and heating mantel. The contents of the flask were stirred and maintained at 50°–60° C. while 31.45 parts of 2-(4'-t-amylbenzoyl)benzoic acid as a 20.75% solution in methylene chloride were added to the flask over a 30 minute period. Methylene chloride distilled off as the 2-(4'-t-amylbenzoyl)benzoic acid solution was added and was collected in a receiver over a one hour period. Then the contents of the flask were heated to 85° C. and held for 5 hours. After the 5 hours the reaction mass was drowned into 1,000 parts of water with stirring while allowing the temperature to rise to 65°–70° C. While at 65°–70° C. the aqueous mixture is extracted with 200 parts of o-dichlorobenzene. The aqueous phase was separated and the organic solution washed with 500 parts of water treated with sufficient 30% aqueous sodium hydroxide to give the aqueous phase after washing a positive test on Brilliant Yellow test paper. The organic solution which contained 2-t-amylanthraquinone was separated and dried over anhydrous calcium chloride. The yield was 25 parts of 2-t-amylanthraquinone or about 85% of the theoretical yield.

EXAMPLE VII

Ring closure of 2-(4'-t-amylbenzoyl)benzoic acid to form 2-t-amylanthraquinone.

Three hundred and thirty parts of 2.0% oleum were added to a 500 ml 4-necked round bottom flask equipped with a stirrer, thermometer, dropping funnel, distillation head, ice water cooled condenser and heating mantel. The contents of the flask were stirred and maintained at 50°–60° C. while 31.45 parts of 2-(4'-t-amylbenzoyl)benzoic acid as a 20.75% solution in methylene chloride were added to the flask over a 30 minute period. Methylene chloride distilled off as the 2(4'-t-amylbenzoyl)benzoic acid solution was added and was collected in a receiver over a one hour period. Then the contents of the flask were heated to 85° C. and held for 5 hours. After the 5 hours the reaction mass was drowned into 1,000 parts of water with stirring while allowing the temperature to rise to 65°–70° C. While at 65°–70° C. the aqueous mixture is extracted with 100 parts of methylene chloride. The aqueous phase was separated and the organic solution washed with 500 parts of water treated with sufficient 30% aqueous sodium hydroxide to give the aqueous phase after washing a positive test on Brilliant Yellow test paper. The organic solution which contained 2-t-amylanthraquinone was separated and dried over anhydrous calcium chloride. The yield was 24.5 parts of 2-t-amylanthraquinone or about 83% of the theoretical yield.

What is claimed is:

1. A process comprising adding one part by weight of an alkylbenzoylbenzoic acid, wherein the alkyl group contains from 2 to 5 carbon atoms as about a 10 to 40% by weight solution in a suitable solvent, to 7 to 15 parts by weight of 100% sulfuric acid or up to 12% oleum, removing the solvent by distillation at from 20° to 60° C., heating at 80° to 95° C. to cause the corresponding alkylanthraquinone to form, drowning the resulting sulfuric acid or oleum solution in water to dilute the sulfuric acid concentration to from 10 to 40% by weight and separating the alkylanthraquinone from the water.

2. The process of claim 1 wherein the alkyl group is t-amyl, t-butyl or ethyl.

3. The process of claim 2 wherein the solvent is methylene chloride.

4. The process of claim 3 wherein the reaction is carried out at from 83° to 87° C.

5. The process of claim 4 wherein the alkylanthraquinone which formed is extracted from the dilute sulfuric acid with a solvent.

6. The process of claim 5 wherein from 9 to 12 parts by weight of sulfuric acid or oleum are present per part by weight of alkylbenzoylbenzoic acid being reacted.

7. The process of claim 6 wherein the step of heating at 83° to 87° C. is carried out for from 3 to 5 hours.

8. The process of claim 7 wherein the extraction solvent is methylene chloride, a chlorinated benzene, an aromatic hydrocarbon solvent boiling at from about 181° to 210° C. or mixtures thereof.

9. The process of claim 8 wherein the alkyl group is t-amyl.

10. The process of claim 8 wherein from a 15 to 30% by weight solution of alkylbenzoylbenzoic acid is used and the sulfuric acid or oleum is diluted to 20 to 30% by weight in the drowning step.

UNITED STATES PATENT OFFICE
CERTIFICATE OF CORRECTION

PATENT NO. : 4,404,140
DATED : Sep. 13, 1983
INVENTOR(S) : William L. Evans

It is certified that error appears in the above-identified patent and that said Letters Patent are hereby corrected as shown below:

In claim 9, line 1, change "claim 8" to read --claim 10--.

Signed and Sealed this

Sixth Day of December 1983

[SEAL]

Attest:

GERALD J. MOSSINGHOFF

Attesting Officer    Commissioner of Patents and Trademarks